(12) United States Patent
Gabriele et al.

(10) Patent No.: US 11,208,627 B2
(45) Date of Patent: Dec. 28, 2021

(54) AUGMENTED BIOCONTAINMENT MATERIALS AND AUGMENTED BIOCONTAINMENT ENCLOSURES

(71) Applicant: THE SECANT GROUP, LLC, Telford, PA (US)

(72) Inventors: Peter D. Gabriele, Frisco, TX (US); Jeremy J. Harris, Doylestown, PA (US); Charles Brendan Nicholson, Perkasie, PA (US); Steven Lu, Ambler, PA (US); Jeffrey H. Robertson, Sellersville, PA (US); Gael Peron, Winston-Salem, NC (US)

(73) Assignee: THE SECANT GROUP, LLC, Telford, PA (US)

( * ) Notice: Subject to any disclaimer, the term of this patent is extended or adjusted under 35 U.S.C. 154(b) by 246 days.

(21) Appl. No.: 16/250,457

(22) Filed: Jan. 17, 2019

(65) Prior Publication Data

US 2019/0218507 A1   Jul. 18, 2019

Related U.S. Application Data

(60) Provisional application No. 62/618,419, filed on Jan. 17, 2018.

(51) Int. Cl.
| | |
|---|---|
| *C12N 5/00* | (2006.01) |
| *C12M 1/00* | (2006.01) |
| *C12M 1/12* | (2006.01) |
| *C12M 1/34* | (2006.01) |

(52) U.S. Cl.
CPC ........... *C12N 5/0068* (2013.01); *C12M 23/14* (2013.01); *C12M 23/20* (2013.01); *C12M 23/26* (2013.01); *C12M 23/28* (2013.01); *C12M 23/52* (2013.01); *C12M 25/14* (2013.01); *C12M 41/46* (2013.01); *C12N 2533/30* (2013.01)

(58) Field of Classification Search
CPC combination set(s) only.
See application file for complete search history.

(56) References Cited

U.S. PATENT DOCUMENTS

| | | | |
|---|---|---|---|
| 7,722,894 B2 | 5/2010 | Wang et al. | |
| 9,359,472 B2 | 6/2016 | Nicholson et al. | |
| 2006/0270023 A1* | 11/2006 | LeDuc | C12M 25/02 |
| | | | 435/289.1 |
| 2013/0231412 A1 | 9/2013 | Langer et al. | |
| 2015/0094796 A1 | 4/2015 | Matheny | |
| 2015/0344618 A1 | 12/2015 | Nicholson et al. | |
| 2016/0143738 A1* | 5/2016 | Matheny | A61L 27/54 |
| | | | 623/23.72 |

FOREIGN PATENT DOCUMENTS

| | | |
|---|---|---|
| WO | 2004094586 A2 | 4/2004 |
| WO | 2017164992 A2 | 9/2017 |

OTHER PUBLICATIONS

Frydrych, M. et al., Polymer 2017, vo. 122, pp. 159-168.*
Zhengwei You, Haiping Cao, Jin Gao, Paul H. Shin, Billy W. Day and Yadong Wang, "A functionalizable polyester with free hydroxyl groups and tunable physiochemical and biological properties", Biomaterials vol. 31 (2010) pp. 3129-3138.

* cited by examiner

*Primary Examiner* — Heidi Reese
(74) *Attorney, Agent, or Firm* — McNees Wallace & Nurick LLC

(57) ABSTRACT

A biocontainment vessel includes a vessel structure including a structural composition and an enhancement composition associated with the structural composition. The enhancement composition includes a co-polymer. The co-polymer is a poly(glycerol sebacate) or a poly(glycerol sebacate urethane). The enhancement composition may also include an augmentation agent associated with the co-polymer. The enhancement composition is located with respect to the structural composition such that the enhancement composition benefits biological cells contained in the biocontainment vessel. A composition includes a co-polymer and an augmentation agent contained by the co-polymer. A method of containing biological cells includes placing the biological cells in an augmented biocontainment vessel and storing them in the augmented biocontainment vessel under predetermined conditions. An augmented substrate includes a substrate and an enhancement composition coating a surface of the substrate.

27 Claims, 2 Drawing Sheets

AUGMENTED BIOCONTAINMENT MATERIALS AND AUGMENTED BIOCONTAINMENT ENCLOSURES

CROSS-REFERENCE TO RELATED APPLICATIONS

This application claims priority to and the benefit of U.S. Provisional Application No. 62/618,419 filed Jan. 17, 2018, which is hereby incorporated by reference in its entirety.

FIELD OF THE INVENTION

This application is directed to biocontainment and cell culture. More specifically, this application is directed to augmented biocontainment materials, augmented biocontainment enclosures, and methods for making and using the same.

BACKGROUND OF THE INVENTION

Disposable bioreactors and storage containment devices for living cells of various types are conventionally based on man-made polymers, and in most cases polymer films, assembled into bags or assemblies that have characteristics of volume, but these polymers and associated materials of construction expose the cell culture or cell load to non-biocompatible, fugitive, and potentially toxic materials.

Current technology limitations raise two important questions about cell culture, cell expansion, and blood storage and biologic cell containment in cell culture research. First, to what temporal extent do blood cells and tissue cells maintain their intended or innate function in man-made storage containment, where they are cultivated in an artificial ex vivo environment, and remain viable to deliver an efficacious therapy? Second, what are the unseen secondary effects of ex vivo cultivation in man-made polymeric containment, and can these secondary effects be eliminated in man-made materials in contact with cells that dictate the medical sequelae of toxic metabolic substances, contamination of cultures from materials of construction, or the milieu of personalized biochemistry of the donor to the patient treatment?

The polymeric surface and the indigenous polymer chemistries of many materials conventionally used in the construction of bioreactors are not optimum. Examples include polyvinyl chloride (PVC) and polyethylene terephthalate (PET) plasticized with phthalate esters, which are known to be cancer-causing.

Attempts have been made to improve standard materials of construction. Conventional material attempting to modify surfaces use, for instance, polymeric lactides and glycolides as biodegradable vehicles and resins for such modifications. Lactide and glycolide biodegradable polymers biodegrade into "anaerobic" waste by-products that cell systems must mitigate in their environments. Therefore, the conventional use or "gravitation" to polyglycolic acid (PGA), polylactic acid (PLA), or poly(lactic-co-glycolic) acid (PLGA) as a biodegradable resin is also not ideal. One problem is that degradation of the lactide and glycolide, like certain other "biodegradable polymers", results in breakdown products that are considered antagonistic cellular waste and require an immunologic response to "neutralize" the by-product effects, a biological response that is unavailable in vitro.

BRIEF DESCRIPTION OF THE INVENTION

It would be desirable to create biocompatible surfaces and release mechanisms, to mitigate noxious environmental components having adverse interactions with living systems, and to advance improvements in cell culture viability, bioreactor constructs for cell culture, support, and development, and storage related to cell therapeutics, blood storage, microbial culture, and/or tissue engineering.

Similarly, it would be desirable to improve cell culture viability, bioreactor constructs for cell culture, and/or cell support, cell development, and/or cell storage related to somatic, stem, and/or microbiological cell therapeutics, blood storage, microbial culture, and/or tissue engineering.

In an embodiment, a biocontainment vessel includes a vessel structure including a structural composition and an enhancement composition associated with the structural composition. The enhancement composition includes a co-polymer. The co-polymer is a poly(glycerol sebacate) or a poly(glycerol sebacate urethane).

In another embodiment, a composition includes a co-polymer and an augmentation agent contained by the co-polymer. The co-polymer is a poly(glycerol sebacate) or a poly(glycerol sebacate urethane).

In yet another embodiment, a method of containing biological cells includes placing the biological cells in an augmented biocontainment vessel. The method also includes storing the biological cells in the augmented biocontainment vessel under predetermined conditions.

In another embodiment, an augmented substrate includes a substrate and an enhancement composition coating a surface of the substrate.

Various features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
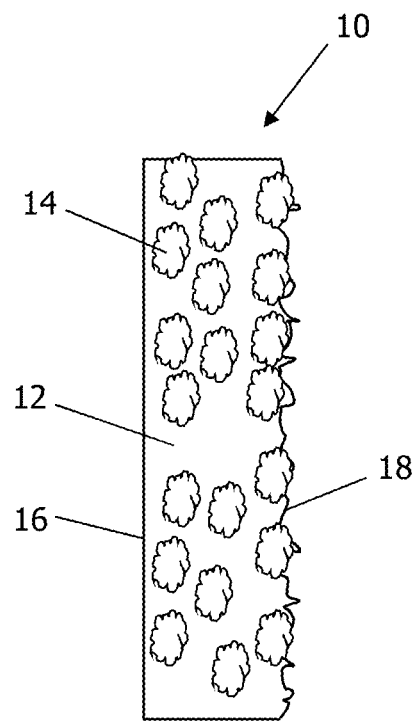
FIG. 1 shows a schematic cross section of a biocontainment vessel augmented with a PGS or poly(glycerol sebacate urethane) (PGSU) plasticizer in an embodiment of the present disclosure.

Augmented biocontainment vessels for controlled storage, for cell expansion for therapy, and for general protection include constructions for the improvement and enhancement of cellular maintenance in storage, culture incubation, or expansion, where cellular environments require management of cell viability and reduction of adverse transfer of toxic components or by-products.

The embodiments described herein may include an article of manufacture, a composition of matter, methods of using, and/or methods for forming or using the same. Preferred embodiments may include biocompatible surfaces, release mechanisms, and mitigation of noxious environmental components having adverse interactions with living systems.

Benefits may include improved artificial polymer-based bioreactors and storage containment. Many man-made polymeric materials have non-cyto-compatible surfaces that inadvertently expose or produce fugitive (indigenous) debris at these surfaces, counteracting environments that attempt to biomimic a natural environment. Present embodiments may create pristine, cell-compatible environments similar to natural incubation as well as improving permanent glass reactors, thereby enhancing the cell environment.

A composition includes a biofriendly polymer and an augmentation agent contained by, or otherwise associated with, the biofriendly polymer. In some embodiments, the augmentation agent is physically mixed with the biofriendly polymer. In some embodiments, the augmentation agent is chemically attached to the biofriendly polymer. The composition is preferably in a solid or substantially solid state and is free or substantially free of solvent. In some embodiments, the composition is used in an augmented biocontainment vessel.

Biofriendly polymers may support the engineering changes required for the construction of bioreactors. In some embodiments, the biofriendly polymers are co-polymers. In some embodiments, the co-polymers are poly(glycerol sebacate) (PGS) and/or poly(glycerol sebacate urethane) (PGSU) and associated co-polymers of glycerol esters of fatty and diacids, which are desirable candidates to support surface modifications. These, as well as new resins for extrusion and consequently films for containment construction, may be derived from these chemistries for use as engineering films or surface treatments either as coatings or for polymer annealing.

In some embodiments, the biofriendly polymer contains one or more augmentation agents, which may be covalently attached to the biofriendly polymer or physically mixed in with the biofriendly polymer. The augmentation agent positively contributes to cell life or provides at least one biological benefit to cells, either by being located on the surface of the biofriendly polymer or upon release of the augmentation agent from the biofriendly polymer. Functions of the augmentation agent may include, but are not limited to, providing nutrition, preventing coagulation, and/or scavenging lactic acid. In some embodiments, the augmentation agent functionally modifies the biofriendly polymer.

The augmentation agent may include, but is not limited to, a cell nutrient; a 2-3-diphosphoglycerate scavenger; a composition protecting against hemoglobin scavenging of nitrous oxide such as, for example, a stabilized hemoglobin protease, heme lipase, heme metalloprotease, or amino peptidases specific for hemoglobin; an affinity composition for toxins such as, for example, chelating agents or charged chemistries such as, for example, zwitterion entities; a fiber extrudate having specific enzymatic activity for hemoglobin; a paramagnetic material such as, for example, super paramagnetic iron oxide and other paramagnetic metals; a lactic acid scavenger through lactate dehydrogenase denaturation and other mechanisms to preserve aerobic respiration in storage including confined $O_2$ within polymer matrices including microparticles containing calcium peroxide and sodium percarbonate and other $O_2$-releasing oxides that may be bound to the film surface, incorporated by way of microparticle dispersion within the matrix, or dispersed within the polymer, the idea being that available $O_2$ within the storage containment avoids anaerobic pathways leading to lactic acid production; a cell preservation composition such as, for example, citric acid and citric acid compositions with amino acids such as, for example, arginine, adenosine, and adenine; an anti-coagulation composition such as, for example, citric acid, phosphate, dextrose, and adenine (CPDA); a sanitation composition such as, for example, a biocide, an antibiotic, or a biostatic compound; a surface passivation composition that mitigates pH shifting or reduces surface energy to minimize cell attachment to sidewalls; or combinations thereof.

Certain biocontainment embodiments are contemplated, including, but not limited to, manipulations of surfaces, materials of construction, or designed mechanisms, to improve biocontainment vessels.

FIG. 1 through FIG. 4 show approaches for producing a formulated coating or layer on a low-cost film, glass, or plastic, a reservoir within a low-cost film, or the reformulation and compounding of polymer raw resin components used in the extrusion and development of enhanced polymer films or plastic structures.

FIG. 1 shows one embodiment of an augmented biocontainment vessel 10 including a structural composition 12 and an enhancement composition 14. The outer surface 16 of the augmented biocontainment vessel 10 is shown as relatively smooth and the inner surface 18, which is on the containment side of the augmented biocontainment vessel 10, is shown as relatively rough compared to the outer surface 16, but either may be rough or smooth. In an exemplary embodiment, the enhancement composition 14 is PGS or PGSU used as a plasticizer in the augmented biocontainment vessel 10. In an exemplary embodiment, the augmented biocontainment vessel 10 is a blood bag with polyvinyl chloride (PVC) as the bulk plastic for the structural composition 12.

Figure 2:
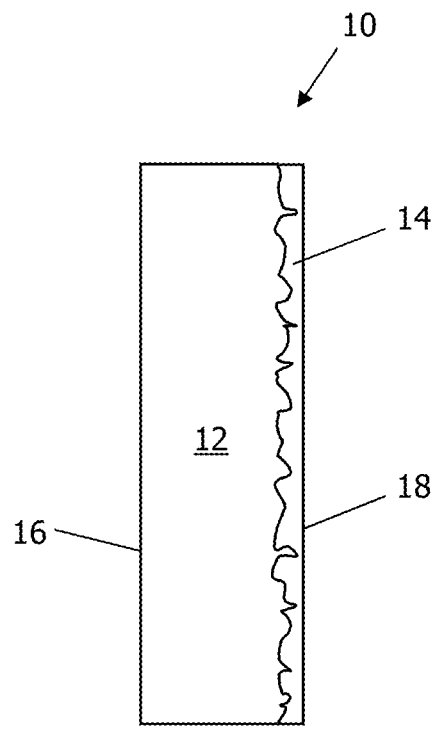
FIG. 2 shows a schematic cross section of a biocontainment vessel augmented with a coating in an embodiment of the present disclosure.

FIG. 2 shows another embodiment of an augmented biocontainment vessel 10. In this embodiment, the enhancement composition 14 is a layer on the structural composition 12 on the containment side of the augmented biocontainment vessel 10. Although the outer surface 16 of the augmented biocontainment vessel 10 and the inner surface 18, which is on the containment side of the augmented biocontainment vessel 10, are shown as relatively smooth and the containment side surface of the structural composition 12 is shown as relatively rough compared to the outer surface 16 and inner surface 18, each may independently be rough or smooth. The inner surface 18 of the augmented biocontainment vessel 10 may be provided by the enhancement composition 14 to have a roughness similar to or different from the roughness of the containment side of the structural composition 12.

In an exemplary embodiment, the structural composition 12 includes PGSU as a bulk material in the augmented biocontainment vessel 10. The enhancement composition 14 is a coating on the structural composition 12 and forms the inner surface 18 of the augmented biocontainment vessel 10, whereas the outer surface 16 is uncoated. The enhancement composition 14 includes a nutrient-containing or functionally-modified PGS (NPGS). The containment-side surface of the structural composition 12 is shown as rough in FIG. 2 but is preferably smooth in this embodiment.

In another exemplary embodiment, the structural composition 12 includes a low-cost stock film or PVC with the outer surface 16 being uncoated. The enhancement composition 14 includes PGS or PGSU and may be provided as a coating, a film, a co-extruded layer, a polymer surface modification, or by coupling agent chemistry to the bulk material. The enhancement composition 14 may provide the augmented biocontainment vessel 10 with passivation, nutrients, a barrier, preservation, and/or anticoagulation.

In yet another exemplary embodiment, the structural composition 12 includes a low-cost stock film or PVC as a bulk material of the augmented biocontainment vessel 10.

The enhancement composition 14 is a coating on the structural composition 12 that forms the inner surface 18 of the augmented biocontainment vessel 10, whereas the outer surface 16 is uncoated. The enhancement composition 14 includes an NPGS or a nutrient-containing or functionally-modified PGSU (NPGSU). The functional modification may be a preservation component, an anticoagulation component, citric acid, phosphate, dextrose, and/or adenine.

Figure 3:
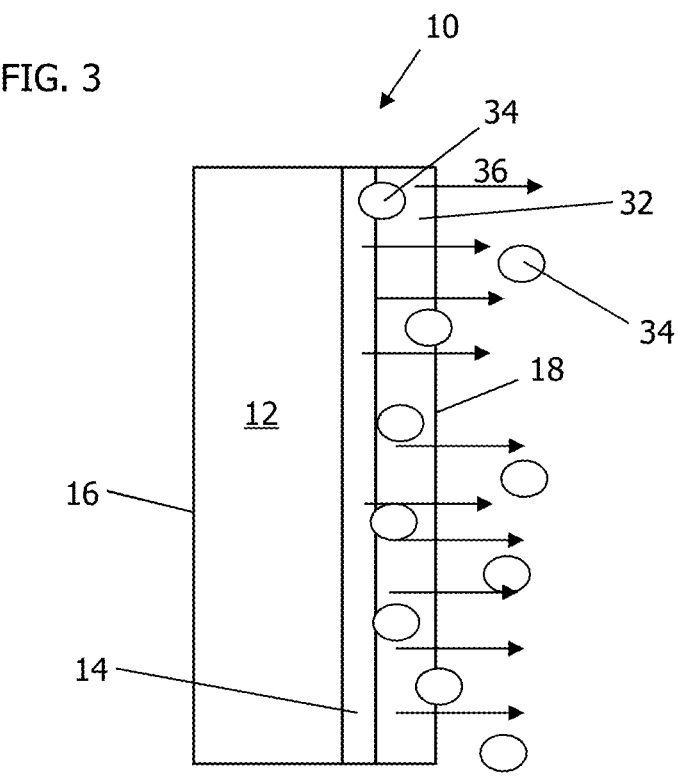
FIG. 3 shows a schematic cross section of a double-layered containment film with a reservoir layer between the two film layers in an embodiment of the present disclosure.

FIG. 3 shows another embodiment of an augmented biocontainment vessel 10. The augmented biocontainment vessel 10 includes an enhancement composition 14 as a reservoir layer on the containment side of a structural composition 12. The augmented biocontainment vessel 10 further includes an inner film layer 32 on the containment side of the enhancement composition 14 and providing the inner surface 18. The enhancement composition 14 includes NPGS or NPGSU. The structural composition 12, the enhancement composition 14, and the inner film layer 32 may be coextruded or otherwise formed next to each other. The nutrients or functional modifications 34 in the enhancement composition 14 may travel 36 from the enhancement composition 14 through the inner film layer 32 by active diffusion to be released into the interior of the augmented biocontainment vessel 10 at the inner surface 18.

The structural composition 12 in FIG. 3 may include, but is not limited to, polymers or biopolymers composed of metabolic building blocks including, but not limited to, carbohydrate, small chain fatty acid, sugar, amino acid, oligomeric protein, functional group chemistries that are nonimmunogenic or may provide nutritional support, and combinations thereof as monomeric units. Appropriate polymer may also include manmade polymers void of toxic catalysts and characterized by thermoplastic features including elastomeric properties such as, for example, vinyls, urethanes, and polyesters. Catalysis may be driven by physical means such as, for example, high energy radiation, thermal conversion, ultraviolet (UV), infrared (IR), X-ray, gamma to drive initiator-free free radical polymerization, polycondensation, acid-base, and/or redox reactions.

Figure 4:
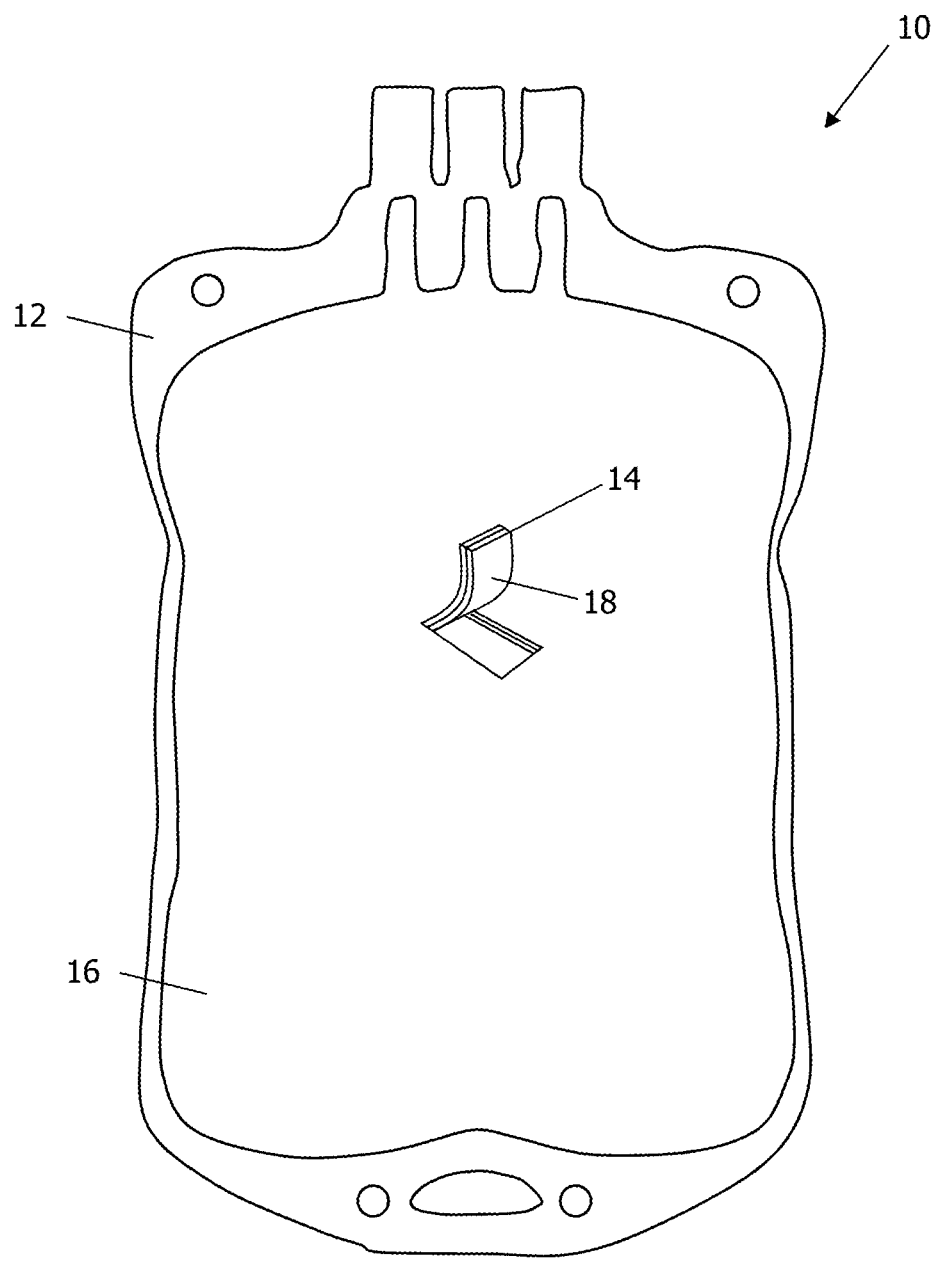
FIG. 4 is a perspective view of the augmented biocontainment vessel of FIG. 2.

FIG. 4 shows a partial perspective view of the augmented biocontainment vessel 10 of FIG. 2 in the form of a blood bag. The augmented biocontainment vessel 10 includes a vessel structure defining an enclosed or contained space. An enhancement composition 14 on one side of the augmented biocontainment vessel 10 provides the inner surface 18 of the augmented biocontainment vessel 10, whereas the outer surface 16 provided by the structural composition 12 is uncoated. The enhancement composition 14 may include PGS or PGSU and may be provided as a coating, a film, a co-extruded layer, a polymer surface modification, or by coupling agent chemistry to the structural composition 12. Any of the vessel embodiments of FIGS. 1, 2, and 3 may have such a shape or any other appropriate biocontainment vessel shape.

In some embodiments, a surface modification of a film of a biocontainment vessel improves the topography, improves the physiology, provides nutrition, or provides protection.

Cells in culture often adhere to reactor side-walls. Polymer films may be physically modified or chemically treated to provide a mechanism that may prevent adhesion or may release essential components into the culture media from the interior walls of the containment device.

Comparative scanning electron microscopy (SEM) surface analysis has shown that the interior topography of a surface may adversely influence thrombogenic action by having an impact on cell membrane shearing. Exemplary embodiments may create non-thrombogenic surfaces.

Not all cells respire or metabolize in the same manner, and therefore not all cells expand in the same manner. Consequently, cell-specific bioreactors and cell storage containment devices of custom additive design or specialized surface modification for the physiology of the cell are desirable.

Living cells in containment metabolize. Under certain conditions, aerobic respiration may shift to anaerobic respiration. Shifts may be the result of low $O_2$ tension and/or depletion of necessary metabolites. Containment walls may be thought of as "pantry shelves", where both metabolites and gases may be exchanged. Here the interior containment walls may be treated as reservoirs of nutrition and cell support. In some embodiments, a film containing nutrient support is co-extruded with one or more base films to provide the custom surface. Containment walls may be configured with a free-energy of diffusion mechanism of release of growth components, much like transdermal reservoirs. Likewise, controlled release and augmented stimulated release mechanisms may be integrated using heat, light, and/or electromagnetic radiation.

In addition to nutrition, containment surfaces may protect the contents from deterioration or cell death by autoimmune response. For instance, anticoagulants and preservatives may be embedded into contact films such that the essential components either fugitively migrate into the culture or are released by stimulated release or controlled degradation.

In some embodiments, a surface coating transforms the functionality of a film.

Coatings and surface treatments are a simple way of transforming a non-biocompatible surface into a biocompatible surface. Coatings may be considered as vehicles that in the culture environment may deliver a plurality of essential components or transform a non-biocompatible surface into a biocompatible surface through barrier passivation.

In some embodiments, polymer compounding provides a new material of construction for film resins. Polymer resins may be compounded with essential components that may be released from the interior walls of the containment device during storage or incubation. Surface coating of interior film walls is an alternative to compounding essential physiological and nutritional agents into the film polymer structure.

Polymer films may be considered 3-D structures at the molecular level that may modify the film's incubation function with engineering properties or hold onto additives and essential components for delivery into the culture medium for cell survival. These additives and essential components may include, but are not limited to, plasticizers, nutritional compounds, active pharmaceutical ingredients (APIs), biologics, active small molecules not considered drugs, preservatives, gases, or antioxidants.

In some embodiments, polymer synthesis provides new materials of construction for films and coating vehicles.

General-use film stock in the disposable biocontainment industry has not had a custom designed material for the biocontainment use. Like most things in the medical device field, these materials of construction are borrowed and with the borrowing comes the contending with cytocompatibility issues.

Polymeric film stock may, however, be developed having not only the engineering properties required for fabrication but also the matrix purity for biocompatibility. For instance, a pristine polymer may be developed that is process-compounded with metabolites to eliminate any toxic or detrimental effect to the contained cells, should material migrate or bloom from the surface of the films.

In some embodiments, a biocontainment enhancement provides smart containment. Electronic and photonic integration into film composite structures may create "intelligent" systems that may monitor and analyze in real time. Lab-on-a-chip technology may be integrated into film stock to provide process control, as well as essential physiological and biological information.

In one embodiment, a classic passive or neutral interior containment volume constructed from man-made materials is transformed to include active surfaces that may be customized to provide the cultured cells or stored cells with essential biochemistry or mechano-biologic conditions.

In some embodiments, a multitude of reactor and storage container configurations include modified surfaces to address specific biological needs or consequences. These surfaces modified by coatings and films may be specifically designed for the intended and specific use in culture and storage. In contrast, most of the containment industry relies on materials that are normally used for other biomedical or industrial uses.

In some embodiments, existing film surfaces from standard stocks are modified or activated to accept such coatings. Coating vehicles may be derived from specialized biocompatible resin vehicles, such as PGS, PGSU, or co-polymers of such, that provide bio-inertness or bio-stimulation depending upon the mechanism in use. For instance, PGS monomers are metabolites and as such the breakdown by-products of PGS may provide components to the Krebs cycle. On the other hand, the benign nature of the glycerol esters may also permit their use as controlled release matrices. Coatings may act as passivation or scavenger surfaces when formulated with counterion or polymer affinity functionality.

Films may be compounded and formulated for extrusion to create wall structures, either as stand-alone or composite surfaces, to the interior that deliver a specific requirement or service preservation. Compounded films may also act as constructed composites that hold materials as a reservoir.

In some embodiments, chemical and/or physical film modifications, including reformation compounding based on film chemistry and surface science, provide biocontainment for integration into cell contact and interfacial stability.

In one embodiment, PGS is incorporated as a "non-phthalate" plasticizer for PVC and polyurethane (PU) film stock. In another embodiment, a compounded resin system as a film stock includes PGSU derived from PGS for biocompatibility in cell contact interfacing. In yet another embodiment, smart materials for containment monitoring and management may include diagnostic systems such as active (integrated circuit-based technology) and passive (chemistry-based technology) diagnostic systems.

In some embodiments, biocontainment enhancements include polymer resin and coating vehicles, such as PGS resin and modifications for web stock coating.

In one embodiment, PGS is formulated as an anti-coagulant, an anti-adhesion composition, a self-"cleaning" film coating, or a combination thereof. The PGS may act as a backbone vehicle support for anchored nutrient and additive film coatings, such as, for example, with components like citrate phosphate dextrose adenine (CPDA) solution or citrate phosphate dextrose (CPD) solution for anticoagulation blood storage. In another embodiment, PGS serves as a nutrient support, a passivation layer, and/or a barrier film coating modification to support cell survival and culture and use of stock film.

In one embodiment, the use of PGS or PGS and co-polymers and crosslink options may be preferred in the case of coatings technology. Without wishing to be bound by theory, the coating may passivate harmful chemistry from the interior wall and provide a biocompatible and bioactive surface to the benefit of the culture or storage needs.

In another embodiment, the use of PGS or PGS and co-polymers and crosslink options may be preferred in the case of film technology. Films and film-like technologies such as, for example, sputter coats, lacquers, passivation treatments, and coupling aged fixation may serve as barrier coating layers to prevent fugitive loss of toxic materials into containment vessels. Without wishing to be bound by theory, the developed film is a polymer option as a new material of construction that passivates harmful chemistry from the interior wall and provides a biocompatible and bioactive surface to the benefit of the culture or storage needs.

In one embodiment, PGS resin vehicles are based on specific molecular weight (MW) and stoichiometric variations of metabolite monomers for coatings formulated with specialized culture media requirements for treatment of containment interiors for nutrition, for buffering, for preservation or homeostatic development, for red blood cell (RBC) transfusion and storage, for progenitor cell expansion and monitoring of culture processes for cell therapy, for somatic cell tissue engineering and organ regeneration, or combinations thereof. In some such embodiments, the device may be an "instant" media single-use device characterized by just adding water to provide nutrient support that originates from the containment walls. The wall nutrition may be in the form of "dehydrated" compositions, where a wall coating converts to media support or media compositions.

In another embodiment, high-MW PGS extrusion resins and co-polymers are synthesized, compounded, and formulated with specialized culture media formulations for extruded film stock of containment interiors for nutrition, buffering, preservation, or homeostatic development in RBC transfusion and storage, progenitor expansion and incubation, somatic cell tissue engineering, or combinations thereof. In some embodiments, the high-MW PGS extrusion resin has a weight average molecular weight of at least 25 kilodaltons (kDa), alternatively 25 kDa to 40 kDa, alternatively at least 60 kDa, alternatively 60 kDa to 100 kDa, or any value, range, or sub-range therebetween, to provide solid thermoplastic surfaces.

In another embodiment, non-lactide and/or non-glycolide biodegradable or biocompatible film coating systems are prepared for cell contact mediation and film-wall passivation from standard film stocks to level and remove antagonistic topographies, for barrier film composite construction to block out fugitive toxic polymer additives, or combinations thereof.

In another embodiment, CPDA solution "additives" (citric acid, phosphate, dextrose, and/or adenine/adenosine) are introduced to interior wall coatings or film stock polymers formulated from PGS, PGSU, a co-polymer thereof, or another non-lactide or non-glycolide for preservation, anti-coagulation, nutrition, or combinations thereof.

CPDA solution components all contain functional groups that may be incorporated or reacted into the backbone of PGS, PGSU, or a co-polymer thereof. In another embodiment, one or more CPDA solution components are incorporated into the PGS or PGSU polymer, creating coatings with anchored (polymerized-in) additives to PGS or PGSU. The CPDA-modified resins may be further converted into extrusion resins or coating vehicles for preservation, anti-coagulation, nutrition, self-buffering, or combinations thereof.

Nitrous oxide (NO) is a vasodilator, and hemoglobin (Hgb) scavenges any free NO in collected and stored blood. This aggravates the depletion of NO as blood ages from cell membrane lysing, consequently releasing Hgb. Also, vasoconstriction is antagonistic in blood transfusions, especially for hypovolemic patients. In some embodiments, passivation or a coating for film-wall saturation protects against Hgb scavenging of NO. Likewise in other embodiments, wall reservoirs release or diffuse NO throughout blood storage to counter Hgb action by Hgb saturation with NO.

Blood is collected from a diverse population with varying degrees of blood factors related to hygiene, health, and contamination. In another embodiment, a passive indicator or active integrated electronic or photonic chemical indicator system or lab-on-a-chip is integrated into film stock for blood factor profiling and contaminant identification. Further embodiments include integrated chemical indicator strips or chemo-responsive films, totally smart blood profiling device units, diabetes blood glucose monitors, immunomodulatory markers for disease-specific blood recipients, or combinations thereof.

As blood ages in storage, its metabolic behavior influences its efficacy as an oxygen (O) delivery "device". Blood metabolic by-product chemicals such as 2,3-diphosphoglycerate (2,3-DPG) may antagonize the $O_2$ uptake once transfused to the patient. In some embodiments, indigenous 2,3-DPG film response for metabolic activity includes an "indicator strip" film on a bag for 2,3-DPG, incorporation of a 2,3-DPG scavenger in vessel wall constructs, or combinations thereof.

In another embodiment, a coating is applied to a quick-treatment nutrient bag. Coating vehicles may be considered stock treatments to a formed film material of construction before container assembly. The film surface pretreatment has either a selective affinity or a broad affinity to a solution that may be added to a constructed container immediately prior to use. Such containment vessels may include a pre-activated surface that captures and couples respective treatments as needed on the fly.

A buffy coat is the fraction of an anticoagulated blood sample that contains most of the white blood cells and platelets following density gradient centrifugation of the blood. In another embodiment, a gradient coating on side walls of a container is designed with surface energy properties that have a super-affinity for plasma, the leukocytes and platelets of a buffy coat, and the erythrocytes via surface energy distinction, thereby stabilizing separation. A buffy coat bag may include greater separation efficiencies than achieved by centrifugation.

In another embodiment, a container includes interior gas ($O_2$ and/or NO) diffusion walls. As noted above, creating side-wall NO gas release may mitigate Hgb NO scavenging. Likewise, time-dependent storage of blood depletes $O_2$. Further embodiment may include an NO film diffuser, an $O_2$ film diffuser, or combinations thereof. These diffusers may be separate layers or may be incorporated into a single enhancement composition. For example, the diffusers may be incorporated in microparticles. Alternatively, the diffusers may be part of a matrix chemistry designed to degrade and release NO and/or $O_2$ as a function of activated moisture permeation into a layer or by thermal or radiant activation to initiate release.

In another embodiment, an antimicrobial, non-antibiotic film-wall coating reduces sepsis and transmission of communicable diseases. Likewise, polymers compounded and formulated for extrusion may also serve as an assembly for materials of construction. Further embodiments may include PGS coatings, small chain fatty acid glycerol ester polymer coatings, nanostructure film modification, or combinations thereof.

In another embodiment, a PGS, a PGSU, or a co-polymer thereof fiber coating (cladding) coats a portion of an advanced filtration system. The coating may, for example, be an affinity coating for toxins and/or for biologics separation, harvest, or neutralization. The coating may, for example, be a buffer coating, an Hgb scavenging coating, or a nutrient coating. The coating may be for a "chromatographic" system, an ionic exchange system, a gradient release system, or a material transfer system and release fibers and fiber claddings. In another embodiment, the coating creates a filtration exchange to simulate a kidney-in-a-bag for toxin filtration.

In another embodiment, fiber materials are used in filtration of an apparatus. The fibers may act as support structure for functional coatings that have a selective affinity for biomolecules and a chemistry that allows for scavenging unwanted materials or selective isolation of incorporated materials. The fibers may be important components to composite constructs including coatings.

In another embodiment, PGS, PGSU, or a co-polymer thereof coats extruded fibers of alginates for advanced filtration systems. A fiber extrudate may be prepared based on 100% resin composition.

In another embodiment, the coated component is a hyperbaric bag to "pressurize" cell containment, a pressurized bag, a double-walled, gas-filled bag, a balloon bag with a metabolic gas mixture, or combinations thereof.

RBCs are under constant pressure (120 mm Hg+/−) as blood leaves the heart and travels to the capillaries in a normal in vivo arterial blood environment. Once the RBCs "feel" the 0.0 mm Hg pressure on the venous side of the vascular stream, the RBCs swell, which alters their natural oxygen-bearing homeostasis. Venous blood is not under pressure and does not carry $O_2$. In one embodiment, a device recreates the natural hyperbaric blood environment to mitigate RBC deterioration.

In some embodiments, an electromagnetic (EM) and/or pulsatile beat bag reduces $O_2$ release by RBCs. In one embodiment, the bag pulses either as an individual bag or an external storage device, whereby the blood container is pulsed or designed to simulate cardiovascular pulsatile behavior by contact with or placement in the storage device. In one embodiment, the device electrolytically generates $O_2$ from water. In one embodiment, a specialized EM cryo-device provides EM pulsing in cryostorage to align cells.

Normal cellular in vivo environments expose tissues to sinus electro-cardio potentials and pressure pulsation. When RBCs are stagnant at zero pressure, $O_2$ release accelerates. Without wishing to be bound by theory, extraction of RBCs from their normal hyperbaric, EM exposure is believed to significantly negatively affect their behavior.

In one embodiment, an EM blood preservation bag includes a bag film infused with paramagnetic materials and/or strong dipole materials to enhance the EM field. Appropriate paramagnetic materials may include, but are not limited to, magnesium, sodium, iron, aluminum, or any other metal or element so coordinated to feature a paramagnetic property having available coordination complexes with d and f electrons to respond to field effects. Blood, like all human tissue, is bathed in EM fields in vivo. An EM field has been shown to benefit RBC storage ex vivo. Exemplary containment embodiments simulate the in vivo exposure to EM fields.

Cells produce lactic acid when respiration is shifted from aerobic to anaerobic. In storage, cells continue to metabolize and produce lactic acid, which is considered to be a toxic metabolic by-product. In one embodiment, chemotactic walls of a containment vessel include a lactic acid scavenger. Appropriate lactic acid scavengers may include, but are not limited to, lactase enzymes, lactate dehydrogenase, or any other biomolecules exhibiting Lewis base characteristics. In some embodiments, a containment vessel has an affinity for adsorption or conversion of lactic acid from the culture or fluid environment.

The concepts described herein may be extended to other bio-ecological applications, including, but not limited to, microbiological retrieval and storage and sample storage. The coatings and films disclosed herein may be applied to glass or rigid plastic surfaces such that the standard glass or rigid plastic enclosure is converted to a bioreactor environment providing a plurality of shapes, sizes, and configurations. Coatings that resist cell attachment may serve as environmental anti-fouling coatings. Film resins for molding of coatings with specific affinities or actions, where cell adhesion is to be promoted or cell adhesion is to be avoided, may be useful in prosthetic implants to prevent adverse tissue and cellular obstruction of use. Newly-formulated resins may be designed for micro-extrusion in applications, including, but not limited to, three-dimensional (3-D) printing. Formulated resins may also be used as tissue scaffolds. Coatings that encourage cell proliferation may be considered for use in wound care dressing treatments. Hyperbaric blood storage bags may help in transfusion to patients with low blood volume as well as low blood pressure.

In exemplary embodiments, the PGS resin is formed in a water-mediated reaction following a method described in U.S. Pat. No. 9,359,472, which is hereby incorporated by reference in its entirety.

While the foregoing specification illustrates and describes exemplary embodiments, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A biocontainment vessel comprising:
 a vessel structure comprising:
  a structural composition; and
  an enhancement composition associated with the structural composition, the enhancement composition comprising a co-polymer selected from the group consisting of a poly(glycerol sebacate) and a poly(glycerol sebacate urethane) and an augmentation agent physically mixed with or chemically attached to the co-polymer, wherein the augmentation agent is selected from the group consisting of a 2-3-diphosphoglycerate scavenger, a composition protecting against hemoglobin scavenging of nitrous oxide, an affinity composition for toxins, a fiber extrudate, a paramagnetic material, a lactic acid scavenger, a cell preservation composition, a sanitation composition, a surface passivation composition, and combinations thereof.

2. The biocontainment vessel of claim 1, wherein the structural composition comprises polyvinyl chloride.

3. The biocontainment vessel of claim 1, wherein the enhancement composition is located on a surface of the structural composition on a containment side of the vessel structure.

4. The biocontainment vessel of claim 3 further comprising an inner film layer on a surface of the enhancement composition on a containment side of the vessel structure.

5. The biocontainment vessel of claim 1, wherein the enhancement composition is a plasticizer mixed with the structural composition.

6. The biocontainment vessel of claim 1, wherein the co-polymer is poly(glycerol sebacate).

7. The biocontainment vessel of claim 1, wherein the co-polymer is poly(glycerol sebacate urethane).

8. The biocontainment vessel of claim 1, wherein the enhancement composition is located with respect to the structural composition such that the augmentation agent benefits biological cells contained in the biocontainment vessel.

9. A method of containing biological cells, the method comprising:
 placing the biological cells in the augmented biocontainment vessel of claim 1; and
 storing the biological cells in the augmented biocontainment vessel under predetermined conditions.

10. The method of claim 9, wherein the co-polymer is poly(glycerol sebacate).

11. The method of claim 9, wherein the co-polymer is poly(glycerol sebacate urethane).

12. The method of claim 9, wherein the enhancement composition is located with respect to the structural composition such that the augmentation agent benefits the biological cells contained in the biocontainment vessel.

13. A composition comprising:
 a co-polymer selected from the group consisting of a poly(glycerol sebacate) and a poly(glycerol sebacate urethane); and
 an augmentation agent physically mixed with or chemically attached to the co-polymer, wherein the augmentation agent is selected from the group consisting of a 2-3-diphosphoglycerate scavenger, a composition protecting against hemoglobin scavenging of nitrous oxide, an affinity composition for toxins, a fiber extrudate, a paramagnetic material, a lactic acid scavenger, a cell preservation composition, a sanitation composition, a surface passivation composition, and combinations thereof.

14. The composition of claim 13, wherein the co-polymer is poly(glycerol sebacate).

15. The composition of claim 13, wherein the co-polymer is poly(glycerol sebacate urethane).

16. The composition of claim 13, wherein the augmentation agent is physically mixed with the co-polymer.

17. The composition of claim 13, wherein the augmentation agent is chemically attached to the co-polymer.

18. An augmented substrate comprising:
 a substrate; and
 an enhancement composition coating a surface of the substrate, the enhancement composition comprising a co-polymer selected from the group consisting of a poly(glycerol sebacate) and a poly(glycerol sebacate urethane) and an augmentation agent physically mixed with or chemically attached to the co-polymer, wherein the augmentation agent is selected from the group consisting of a 2-3-diphosphoglycerate scavenger, a composition protecting against hemoglobin scavenging of nitrous oxide, an affinity composition for toxins, a fiber extrudate, a paramagnetic material, a lactic acid scavenger, a cell preservation composition, a sanitation composition, a surface passivation composition, and combinations thereof.

19. The composition of claim 13, wherein the augmentation agent comprises a 2-3-diphosphoglycerate scavenger.

20. The composition of claim 13, wherein the augmentation agent comprises a composition protecting against hemoglobin scavenging of nitrous oxide.

21. The composition of claim 13, wherein the augmentation agent comprises an affinity composition for toxins.

22. The composition of claim 13, wherein the augmentation agent comprises a fiber extrudate.

23. The composition of claim 13, wherein the augmentation agent comprises a paramagnetic material.

24. The composition of claim 13, wherein the augmentation agent comprises a lactic acid scavenger.

25. The composition of claim 13, wherein the augmentation agent comprises a cell preservation composition.

26. The composition of claim 13, wherein the augmentation agent comprises a sanitation composition.

27. The composition of claim 13, wherein the augmentation agent comprises a surface passivation composition.

* * * * *